United States Patent

Billington et al.

Patent Number: 4,514,342
Date of Patent: Apr. 30, 1985

[54] POLYETHYLENICALLY UNSATURATED MONOPHOSPHATES

[75] Inventors: Richard W. Billington, London; Gordon B. Blackwell, Surrey; Terence E. Prodger, Sussex, all of England

[73] Assignee: Dentsply Limited, Surrey, England

[21] Appl. No.: 464,778

[22] Filed: Feb. 7, 1983

[30] Foreign Application Priority Data

Feb. 16, 1982 [GB] United Kingdom ............... 8204511

[51] Int. Cl.$^3$ .................... C07F 9/113; A01K 6/02
[52] U.S. Cl. ................... 260/952; 260/940; 433/228
[58] Field of Search ............. 260/952, 940

[56] References Cited

U.S. PATENT DOCUMENTS

| 3,629,187 | 12/1971 | Waller | 260/41 R |
| 4,292,029 | 9/1981 | Craig et al. | 433/228 |
| 4,368,043 | 1/1983 | Yamauchi et al. | 433/217 |

FOREIGN PATENT DOCUMENTS

| 559648 | 7/1958 | Canada | 260/952 |
| 22535 | 7/1975 | Japan | 260/952 |
| 1488403 | 10/1977 | United Kingdom . | |

*Primary Examiner*—Anton H. Sutto
*Attorney, Agent, or Firm*—Edward J. Hanson, Jr.

[57] ABSTRACT

An adhesion promoter, suitable for improving the adhesion of composite dental material to tooth enamel, comprises a solution in a volatile organic solvent therefor, such as a lower alkanol, of a polyethylenically unsaturated monophosphate or salt thereof, containing a monophosphate radical and at least three ethylenically unsaturated groups (preferably terminal ethylenically unsaturated groups) per molecule. Preferred polyunsaturated phosphates are monophosphates of polyhydric alcohols containing at least four hydroxyl groups per molecule in which at least three hydroxyl groups are esterified with an ethylenically unsaturated carboxylic acid, and especially preferred polyunsaturated phosphates (which are provided as new compounds) are those of the formula:

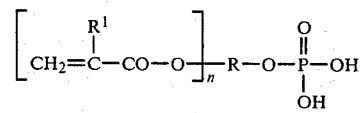

in which:

R is an aliphatic (optionally interrupted by one or more oxygen atoms) cycloaliphatic or aryl radical having a valency of n+1 and containing from 4 to 16 carbon atoms, $R^1$ is a hydrogen atom, alkyl $C_1$-$C_3$, halogen or CN radical, and n is an integer of at least 3, preferably from 3 to 6.

6 Claims, No Drawings

POLYETHYLENICALLY UNSATURATED MONOPHOSPHATES

BACKGROUND OF THE INVENTION

This invention is concerned with improvements in and relating to adhesion promoters, especially for use in promoting the adhesion of addition polymerizable dental materials to natural teeth.

Addition polymerizable dental materials, such as filling materials, cements and the like, generally comprise a mixture of a finely divided filler with one or more ethylenically unsaturated materials capable of in situ polymerization in a dental cavity to form a hard filling material. A wide variety of fillers may be employed and examples thereof include finely divided glasses, ceramics and inorganic oxides contining e.g. silicon and aluminum. The filler will generally have been subjected to an appropriate surface treatment, such as silanation or with a titanate. The finely divided inert filler may form less than 50% by weight of the composite material, but commonly forms from 50 to 85% by weight thereof and especially from 60 to 80% by weight thereof. The inert filler suitably has an average particle size of from 1 to 100, preferably from 1 to 60 microns. Such a filler may be replaced by, or used in admixture with a superfine filler, e.g. having a particle size of from 10 to 400 millimicrons as disclosed in British Patent Specification No. 1,488,403, in which case the filling material may contain lower amount, e.g. 30–50% by weight, of filler.

Other addition polymerizable dental materials comprise a mixture of an organic filler, e.g. a polymer or copolymer of methyl methacrylate, together with an ethylenically unsaturated material, typically methyl methacrylate.

The ethylenically unsaturated component or binder of the composite material generally comprises one or more esters of ethylenically unsaturated carboxylic acids, especially of acryl or methacrylic acid. Thus, the ethylenically unsaturated binder component may comprise simple esters of unsaturated carboxylic acids with monohydric aliphatic alcohols, for example methyl (meth) acrylate, ethyl (meth)acrylate and 2-ethylhexyl (meth) acrylate.

(In this specification the term "(meth)acrylate" is intended to refer to an acrylic or methacrylic acid ester of a hydroxyl group-containing compound.)

Further, the unsaturated component may comprise unsaturated carboxylic esters of polyhydric alcohol, especially polyhydric alcohols containing one or more phenyl groups, such as the adduct of bisphenol A and glycidyl methacrylate, Bisphenol A (meth)acrylate and/or reaction products of 2-hydroxyethyl (meth) acrylate with isophthalic, terephthalic or phthalic acid chloride. Another class of ethylenically unsaturated binder the adducts of 2,2-propane-bis[3-4-phenoxy)-1,2-dihydroxx-propane-1-methacrylate] and an isocyanate or diisocyanate as described in U.S. Pat. No. 3,629,187. Yet another class of ethylenically unsaturated material which may be present in the ethylenically unsaturated binder component comprises the reaction products of monoesters of dihydric alcohols (e.g. ethylene glycol mono(meth)acrylate) with polyisocyanates, especially aliphatic diisocyanates, such as 2,2,4-trimethyl-hexamethylene diisocyanate or hexamethylene diisocyanate. In practice, a mixture of two or more ethylenically unsaturated materials may be, and commonly is, employed.

The unsaturated component may also comprise an unsaturated fluorine-containing material, as disclosed, for example, in U.S. Pat. No. 4,292,029, which additionally serves to reduce penetration of fluids between tooth surfaces and restorative material.

The composite materials should also contain, when filled into a tooth cavity, a polymerization initiator for effecting polymerization of the ethylenically unsaturated binder component. Such initiator should, of course, be capable of initiating polymerization at comparatively low temperatures, i.e. mouth temperatures, and examples of suitable initiators include organic peroxides, such as benzoyl peroxide or tert.butyl peroctanoate, desirably together with an activator, e.g. a tertiary amine activator, such as dimethyl paratoluidine, or ascorbic or sulphinic acid or a salt thereof. In an alternative procedure, the composite filling material may contain an initiator sensitive to visible or ultraviolet light which, on exposure to such light, initiates polymerization of the ethylenically unsaturated binder component. Examples of such initiators include chlorobenzophenone and benzoin methyl ether (for U.V. light) and camphorquinone (for visible light). In some cases, an accelerator, such as a secondary or tertiary amine, may also be employed in order to accelerate the reaction.

It is most desirable, when filling a tooth cavity with a composite filling material, as a dental restorative, to ensure good adhesion between the enamel on the tooth surrounding the cavity and the set (polymerized) composite material since there is thereby obtained a good seal between the set composite material and the enamel of the tooth which prevents, or at least markedly inhibits, ingress of mouth fluids into the filled cavity and so prevents further decay or loss of the filling. In order to achieve good adhesion between the filling material and the tooth enamel, it has been recommended to subject the enamel to an acid etch, for example, with 30–50% aqueous phosphoric acid or 55% aqueous orthophosphoric acid buffered with zinc oxide. This procedure, however, is time-consuming and, naturally, involves the loss or removal of some tooth enamel.

SUMMARY OF THE INVENTION

By an aspect of the present invention, a dental restorative adhesion promoter composition is provided that is suitable for improving the adhesion of a composite dental filling material to tooth enamel. The adhesion promoter is a solution of a polyethylenically unsaturated monophosphate or salt thereof in a volatile organic solvent. The polyethylenically unsaturated monophosphate has a monophosphate radical and at least three ethylenically unsaturated groups per molecule.

The preferred solvent is a lower aliphatic alcohol and the solution is preferably from 0.5 to 10% by weight of the total solution of polyunsaturated phosphate.

The ethylenically unsaturated groups in the polyunsaturated phosphate are preferably terminal ethylenically unsaturated groups.

The polyunsaturated phosphate is preferably the reaction product of a monophosphate of a polyhydric alcohol containing at least four hydroxyl groups in which at least three hydroxyl groups are esterified with an ethylenically unsaturated carboxylic acid.

By another aspect of the invention a method of dental treatment is provided involving polymerizing a dental material comprising a polyethylenically unsaturated material and an initiator therefor in securement with tooth material, the improvement comprising pretreating said tooth material with the polyethylenically unsaturated monophosphate previously described or salt thereof.

By still further aspects of the invention, a dental filling material is provided that includes at least a polymerizable ethylenically unsaturated material, an initiator therefor, an inert filler and a polyethylenically unsaturated monophosphate of the type previously described or salt thereof.

Also an adhesion promoter is provided suitable for improving the adhesion of a free radical polymerizable resin to a substrate. The adhesion promoter is the polyethylenically unsaturated monophosphate or salt thereof previously described. The method of employing the adhesion promoter is also provided.

By another very important aspect of the invention, new compounds are provided that are polyethylenically unsaturated monophosphates of the formula:

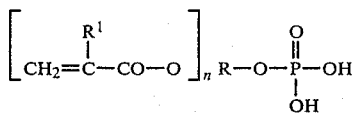

and salts thereof, in which
R is an aliphatic radical (which may be interrupted by one or more oxygen atoms), or a cycloaliphatic radical or aryl radical having a valency of n+1 and containing from 4 to 16 carbon atoms;
$R^1$ is a hydrogen atom, alkyl $C_1$-$C_3$, halogen or CN radical, and
n is an integer of at least 3.

Preferably n is an integer of from 3 to 6 and the compound is chosen from the group consisting of pentaerythritol triacrylate monophosphate, pentaerythritol trimethacrylate monophosphate, dipentaerythritol pentaacrylate monophosphate, and dipentaerythritol pentamethacrylate monophosphate.

DESCRIPTION OF THE PREFERRED EMBODIMENT

It has now been found, in accordance with the present invention, that the adhesion of a composite material, as described above, to tooth enamel may be markedly improved by firstly applying to the tooth enamel a compound comprising a monophosphate radical and at least three ethylenically unsaturated groups. The composite filling material is then introduced into the cavity or cavity preparation and cured therein, with concomitant polymerization of the polyunsaturated phosphate. As a result, it is found that the adhesion of the set composite filling material to the enamel is markedly improved, as compared with a comparable process wherein no polyunsaturated phosphate is employed, and there may be achieved degrees of adhesion comparable to those obtained with prior acid etching of the enamel. In this manner, a dental material can be firmly secured in securement with tooth material.

According to one embodiment of the invention, therefore, there is provided an adhesion promoting composition suitable for improving the adhesion of a composite dental filling material to tooth material comprising a solution, in a volatile organic solvent therefor, of an ethylenically unsaturated monophosphate containing a monophosphate radical and at least three ethylenically unsaturated groups per molecule.

Suitable volatile organic solvents for use in the compositions of the invention include lower aliphatic alcohols, especially ethanol, and the concentration of the ethylenically unsaturated monophosphate in the solution is suitably from 0.5 to 10%, preferably from 0.5 to 2.5%, especially about 1%, by weight.

The ethylenically unsaturated groups in the ethylenically unsaturated monophosphate are preferably terminal or vinyl groups of the formula:

A particularly preferred class of unsaturated phosphates for use in accordance with the invention are monophosphates of polyhydric alcohols containing at least four hydroxyl groups in which at least three hydroxyl groups are esterified with an ethylenically unsaturated carboxylic acid, especially acrylic or methacrylic acid. Thus, one preferred class of polyethylenically unsaturated monophosphate for use in accordance with the invention may be represented by the formula:

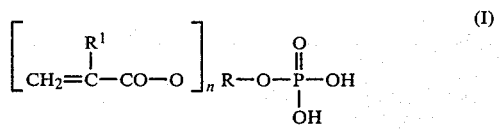

in which,
R is an aliphatic radical (which may be interrupted by one or more oxygen atoms), or a cycloaliphatic radical or aryl radical having a valency of n+1 and containing from 4 to 16 carbon atoms;
$R^1$ is a hydrogen atom, alkyl $C_1$-$C_3$, halogen or CN radical, and
n is an integer of at least 3.
More preferably:
R is an aliphatic radical (which may be interrupted by an oxygen atom), a cycloaliphatic radical or an aryl radical having a valency of n+1 containing from 4 to 16 carbon atoms,
$R^1$ is a hydrogen atom or a methyl group; and
n is an integer of 3 to 6.
Particular examples of such compounds include pentaerythritol tri(meth) acrylate monophosphate and dipentaerythritol penta(meth)acrylate monophosphate. The compounds of formula (I) are in themselves new compounds and are provided as a further feature of the invention.

The compounds of formula (I), and other ethylenically unsaturated monophosphates, may also be used in the form of their salts, for example, alkali metal (e.g. sodium or potassium) or ammonium salts. Polyethylenically unsaturated monophosphates of formula (I) may be prepared by phosphorylating, (e.g. by reaction with phosphorous oxychloride or phosphorous pentoxide) a corresponding monohydroxy compound of the formula:

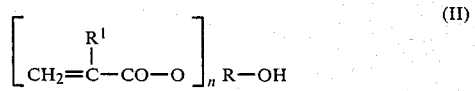

in which R, $R^1$ and n have the meanings defined above.

In some cases adhesion may be enhanced by the use of an intermediate bonding resin, e.g. a polymerized ethylenically unsaturated material containing little or no filler. In this case, the solution of polyunsaturated phosphate is first applied to the tooth material followed by a layer of intermediate bonding resin and finally the filling material is introduced. The intermediate bonding resin may be used before or together with the curing of the filling material.

Further, the adhesion promoters of the invention may be used to improve the adhesion of fissure sealants which are material of similar composition to the intermediate bonding resins noted above.

As noted above, the polyunsaturated phosphates may be employed to improve adhesion between a composite dental filling material and tooth enamel by first applying a composition containing the polyunsaturated phosphate to the tooth enamel and subsequently filling the cavity in the tooth with the filling material. Alternatively, the polyunsaturated phosphate may be incorporated in the filling composition itself and, accordingly, another embodiment of the invention provides a composite dental filling material comprising (i) an inert finely divided filler; (ii) an ethylenically unsaturated binder material; (iii) an initiator for the ethylenically unsaturated binder; and (iv) a polyunsaturated phosphate as defined above, i.e. containing at least three ethylenically unsaturated groups per molecule. In such compositions the proportions and contents of the filler, binder and initiator will be generally conventional and the polyunsaturated phosphate is suitably present in an amount of 1 to 20, preferably from 2 to 5% by weight, based on the total weight of the composite filling. It may be noted that, when present in a composite filling material, the polyunsaturated phosphate may also serve to promote adhesion between the inert filler and the binder, whereby to increase the strength of the cured material. In order to further improve this property, the polyunsaturated phosphate may be coated onto the inert filler before compounding it with the remainder of the ingredients of the composite filling material. When present in a composite filling material, the polyunsaturated phosphate may also serve to promote adhesion between the inert filler and the binder, whereby to increase the strength of the cured material. In order to further improve this property, the polyunsaturated phosphate may be coated onto the inert filler before compounding it with the remainder of the ingredients of the composite filling material.

It should be noted that when the initiator system contains an amine, the polyunsaturated phosphate may react or interfere therewith, thereby reducing the effectiveness of the initiator system. Accordingly, it is generally preferred that the initiator system does not contain an amine. However, this is not the case when the polyunsaturated phosphate is first applied to tooth material to act as an adhesion promoter as discussed above.

As will be appreciated, and in common with conventional composite filling materials, it is generally desirable that the catalyst or initiator be brought into contact with the polymerizable ingredient of the filling material only immediately before introduction of the filling material into a dental cavity. To this end, it is common practice to put up composite filling materials as two-part packs, one part containing the initiator, and the other part containing the accelerator, the inert filler and components being mixed with either or both of these two constituents. Where, however, the materials are intended to be polymerized by light or ultraviolet radiation, the material may be put up as a single pack.

The adhesion promoting compositions of the invention may also be used to improve the adhesion to tooth enamel, of orthodontic appliances when using as adhesives a composite material or a polymerizable composition comprising one or more unsaturated materials, such as are used as binders in composite filling materials.

Thus, for example, the polyunsaturated phosphate may be used as an adhesion promoter for the treatment of enamel to which orthodontic brackets or bands are to be attached or, in periodontics, for the treatment of enamel to which a splint is to be attached. Further, they may be used as adhesion promoters in the buildup of teeth with composite materials and the attachment of acrylic veneers via a composite or unfilled resin for the same purpose. Similarly, they may be used as adhesion promoters in the attachment of single unit pontics to the abutment teeth via a composite or unfilled resin.

It has also been found that the adhesion promoters of the present invention may be used to promote the adhesion of composite materials, as described above, to metal substrates and in this connection can find application in the construction of crowns and bridges in which a polymeric material is bonded to the framework or substrate formed of a metal, such as a chromium/cobalt alloy, a gold/copper alloy or the like.

The adhesion promoter of the invention may also be used to improve the adhesion of adhesive materials containing polymerizable ethylenically unsaturated material to substrates other than tooth material, for example, metallic substrates formed of metals, such as chromium/cobalt alloys, gold/copper alloys or the like.

In order that the invention may be well understood, the following examples are given by way of illustration only:

EXAMPLE 1

Pentaerythritol triacrylate phosphate (PETAP)

A solution of technical pentaerythritol triacrylate (15.2 g) and triethylamine (10.1 g) in dry ether (50 ml) was slowly added with stirring to a solution of phosphorus oxychloride (15.3 g) in dry ether, at 0° C. After stirring for two hours at room temperature, the triethylamine hydrochloride formed was filtered off and the product remaining in solution hydrolysed by addition of the ether solution to water (50 ml) with stirring. The resultant mixture was separated and the separated ether layer was then extracted with sodium carbonate solution. The extract was then acidified and the oily precipitate formed was extracted into ether. The ether extract was dried over magnesium sulphate and the ether was then removed from the dried extraction under reduced pressure to give the title compound as a clear colorless viscous oil, the infra-red absorption spectrum of which shows absorption peaks at 2800–2560; 1730; 1640; 1620; 1270; 1190 and 1060 cm$^{-1}$.

EXAMPLES 2 AND 3

Following the procedure of Example 1, pentaerythritol trimethacrylate phosphate (PETMAP) and dipentaerythyritol pentaacrylate phosphate (DPEPAP) were produced from pentaerythritol triacrylate and dipentaerythritol pentaacrylate, respectively. The two products had infra-red absorption spectra as shown in Table 1.

TABLE 1

| Product | Absorption peaks, cm$^{-1}$ |
|---|---|
| PETMAP | 2600–2560; 1730; 1640, 1295; 1160; 1060; 1020 |
| DPEPAP | 2800–2560; 1730; 1640; 1620; 1300; 1270; 1190; 1060 |

A sample of the PETMAP was converted to its sodium salt (Na PETMAP) by reaction with sodium hydroxide.

Test 1

The effects of the above proposed compounds in improving the adhesion of dental material to teeth were tested as follows:

Extracted human teeth stored in 1% saline containing 1% formaldehyde were ground on a flat glass slab with 600 grit Carborundum powder, to give a flat enamel (or dentine) surface about 4 mm in diameter. This was dried with compressed air and a 1% w/v solution of the polymerizable phosphate ester in absolute ethanol was applied with a fine brush or cotton wool wad; excess material and solvent were blown off with compressed air.

Composite material as described in the example of Patent Specification No. 1401805 was sandwiched between a freshly prepared cylinder formed from the composite (3 mm diameter and approx. 15 mm long) and the prepared tooth surface, and held in place with a 200 g weight. Excess composite was carefully removed and the composite allowed to harden at 37° C. After storage of the samples in water at 37° C. for 24 h, adhesion of the cylinders to the tooth substance was measured by pulling them apart in an Instron Universal Testing Machine at a crosshead speed of 0.01 cm/sec. The results for various treatments are given in Table 2.

By way of comparison the above procedure was repeated except that (i) no polymerizable phosphate was employed, (ii) no polymerizable phosphate was employed but the tooth enamel was first subjected to an acid etch, or (iii) a polymerizable phosphate containing only one ethylenically unsaturated group per molecule was employed (hydroxyethyl methacrylate phosphate HMAP). The results of these tests are also shown in Table 2.

TABLE 2

Adhesion of Composite material to tooth substance

| Treatment | Substrate | Average adhesion MPa | Number of Samples |
|---|---|---|---|
| PETAP | Enamel | 7.6 | 8 |
| PETMAP | Enamel | 8.8 | 7 |
| PETMAP | Dentine | 2.4 | 8 |
| Na PETMAP | Enamel | 8.2 | 8 |
| DPEPAP | Enamel | 7.8 | 8 |
| None | Enamel | 0.19 | 8 |
| Acid Etch | Enamel | 8.1 | 6 |
| HMAP | Enamel | 2.7 | 9 |

Tooth enamel treated as above using a PETMAP-containing adhesion promoter unit showed an average adhesion of 7.6 MPa (for 8 samples), after storage in water at 37° C. for three months.

Test 2

Tests were also conducted to ascertain the degree of protection against leakage afforded by the use of the polymerizable phosphates.

Extracted human teeth were selected for the absence of caries and cracks, coated with nail varnish, and set into resin with the crown exposed. Two diametrically opposed cavities, approximately 3 mm in diameter and extending about 2 mm into the dentine, were prepared in each tooth using a high speed handpiece, then thoroughly cleaned and dried with a dental air/water syringe. A cotton wool wad was used to apply a 1% w/v solution of the polymerizable phosphate ester in absolute ethanol to one cavity tooth, and the solvent evaporated with compressed air.

Composite resin as described above was then placed in the cavity, held under pressure with a matrix strip while it hardened, and finally finished with a medium grit abrasive disc lubricated with Vaseline. The second cavity in the tooth was similarly filled and finished, but without using the phosphate ester pretreatment.

After cycling the teeth for 24 hours between four water baths containing 0.1% acid fuchsin and held at 37°–10°–37°–55° C., with an immersion time in each bath of approximately 2 seconds, the cavities were sectioned and leakage of dye between the composite and tooth substance assessed. For twenty-three teeth, sixteen untreated cavities showed more leakage than their treated counterpart, while only three treated cavities showed greater leakage than their untreated counterpart. Statistical analysis shows that the use of the polymerizable phosphate ester as pretreatment gives a highly significant reduction in marginal leakage.

Test 3

In order to evaluate the effectiveness of the polyunsaturated phosphates as coating materials for inert filler in composite materials, a composite material was produced as disclosed in the example of Patent Specification No. 1401805 except that there was used as inert filler a synthetic hydroxy apatite having a particle size less than of 60 microns. A sample of the composite material was made up and the tensile transverse strength thereof was measured. When using an untreated hydroxy apatite, the transverse tensile strength was about 35 Mpa but when employing one which had been coated by slurrying it with a 1% w/v solution of PETMAP in ethanol and then removing the ethanol under reduced pressure, the transverse tensile strength was about 70 Mpa.

What we claim is:

1. Polyethylenically unsaturated monophosphates of the formula:

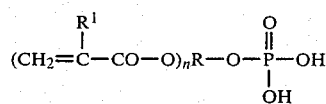

and salts thereof, in which:
R is a pentaerythritol radical having a valency of n+1 and containing from 4 to 16 carbon atoms;
$R^1$ is a hydrogen atom, alkyl $C_1$–$C_3$, halogen or CN radical, and
n is an integer of at least 3.

2. The compound of claim 1 pentaerythritol triacrylate monophosphate.

3. The compound of claim 1 pentaerythritol trimethacrylate monophosphate.

4. The compound of claim 1 dipentaerythritol pentaacrylate monophosphate.

5. The compound of claim 1 dipentaerythritol pentamethacrylate monophosphate.

6. The compounds of claim 1 wherein:
$R^1$ is a hydrogen atom or a methyl group; and
n is an integer of 3 to 6.

* * * * *